United States Patent [19]
Emery et al.

[11] Patent Number: 5,906,826
[45] Date of Patent: *May 25, 1999

[54] METHOD OF INDUCING AN IMMUNE RESPONSE IN A YOUNG ANIMAL

[75] Inventors: Daryll A. Emery; Darren E. Straub; Richard Huisinga, all of Willmar, Minn.

[73] Assignee: Willmar Poultry Company, Inc., Willmar, Minn.

[*] Notice: This patent issued on a continued prosecution application filed under 37 CFR 1.53(d), and is subject to the twenty year patent term provisions of 35 U.S.C. 154(a)(2).

This patent is subject to a terminal disclaimer.

[21] Appl. No.: 08/626,849

[22] Filed: Apr. 3, 1996

Related U.S. Application Data

[63] Continuation of application No. 08/272,116, Jul. 7, 1994, Pat. No. 5,538,733.

[51] Int. Cl.⁶ .......................... A61K 39/02; A61K 39/12; A61K 39/00
[52] U.S. Cl. ........................... 424/422; 424/423; 424/426; 424/184.1; 424/204.1; 424/206.1; 424/211.1; 424/216.1; 424/234.1; 424/243.1; 424/244.1; 424/247.1; 424/252.1; 424/257.1; 424/258.1; 424/259.1; 424/260.1; 424/274.1
[58] Field of Search .................................. 424/422, 423, 424/426, 184.11, 131.1, 204.1, 206.1, 211.1, 214.1, 216.1, 213.1, 220.1, 222.1, 229.1, 207.1, 234.1, 237.1, 239.1, 240.1, 241.1, 257.1, 258.1, 259.1, 274.1

[56] References Cited

U.S. PATENT DOCUMENTS

| | | | |
|---|---|---|---|
| 3,887,699 | 6/1975 | Yolles | 424/19 |
| 3,975,350 | 8/1976 | Hudgin et al. | 260/304 |
| 4,180,560 | 12/1979 | Katz et al. | 424/21 |
| 4,326,523 | 4/1982 | Wolfrom et al. | 128/260 |

(List continued on next page.)

FOREIGN PATENT DOCUMENTS

| | | |
|---|---|---|
| 0 308 197 A2 | 3/1989 | European Pat. Off. . |
| 88/02262 | 4/1988 | WIPO . |
| 95/07290 | 3/1995 | WIPO . |

OTHER PUBLICATIONS

Bhogal, et al., "Anti–Idiotypes as Potential Vaccines and Immunomodulators Against Poultry Disease", *Crit. Rev. Poultry Biol.*, 3, 53–68 (1991).

Bhogal, et al., "Anti–Idiotypic Antibody with Potential Use as an *Eimeria tenella* Sporozoite Antigen Surrogate for Vaccination of Chickens against Coccidiosis", *Infection and Immunity*, 56(5), 1113–1119 (1988).

Francis, et al., "Immunological Priming With Synthetic Peptides of Foot–and–Mouth Disease Virus", *J. Gen. Virol.*, 66, 2347–2354 (1985).

Garnier, et al., "Enhancement of in vivo and in vitro T Cell Response Against Measles Virus Haemagglutinin After its Incorporation into Liposomes: Effect of the Phospholipid Composition", *Vaccine*, 9, 340–345 (1991).

(List continued on next page.)

*Primary Examiner*—Gollamudi S. Kishore
*Attorney, Agent, or Firm*—Merchant, Gould, Smith, Edell, Welter & Schmidt, P.C.

[57] ABSTRACT

The invention provides a method of priming an immune response in the presence of maternal antibody in a young animal by administering to a 1–90 day old animal, a biocompatible and non-toxic solid phase implant containing an immunogenic agent. A preferred implant according to the invention is one that becomes gradually disintegrated in situ the animal. The implant provides for extended sustained delivery of the immunogenic agent into surrounding tissue fluids in the presence of circulating maternal antibodies to provide a priming dose of the immunogenic agent to stimulate substantially immediate antibody production for active immunity against a pathogen when passive protection is no longer provided by circulating maternal antibodies.

24 Claims, 8 Drawing Sheets

U.S. PATENT DOCUMENTS

| | | | |
|---|---|---|---|
| 4,452,775 | 6/1984 | Kent | 424/19 |
| 4,680,174 | 7/1987 | Jarvis, Jr. et al. . | |
| 4,711,782 | 12/1987 | Okada | 424/455 |
| 4,732,155 | 3/1988 | Zetter et al. . | |
| 4,732,971 | 3/1988 | DiMarchi et al. | 530/324 |
| 4,748,018 | 5/1988 | Stolle et al. | 424/87 |
| 4,756,907 | 7/1988 | Beck | 424/85 |
| 4,795,635 | 1/1989 | Peleg et al. | 426/89 |
| 4,863,735 | 9/1989 | Kohn et al. | 424/422 |
| 5,015,476 | 5/1991 | Cochrum et al. . | |
| 5,026,365 | 6/1991 | Rossini et al. . | |
| 5,100,662 | 3/1992 | Bolcsak et al. | 424/88 |
| 5,114,719 | 5/1992 | Sabel et al. | 424/422 |
| 5,153,002 | 10/1992 | McMullen | 424/473 |
| 5,271,945 | 12/1993 | Yoshioka et al. | 424/489 |
| 5,352,448 | 10/1994 | Bowersock | 424/438 |
| 5,538,733 | 7/1996 | Emery | 424/422 |

OTHER PUBLICATIONS

Harlow, et al., *Antibodies, A Laboratory Manual*, generally and Chapter 5, particularly pp. 72–87, Cold Spring Harbor, New York, NY (1988).

Hudson, et al., *Practical Immunology*, Chapter 13, Blackwell Scientific Publications, Oxford, England (1989).

Kohn, et al., "Single–Step Immunization Using a Controlled Release, Biodegradable Polymer with Sustained Adjuvant Activity", *J. Immunological Methods, 95*, 31–38 (1986).

Lerner, et al. "Chemicaly Synthesized Peptides Predicted From the Nucleotide Sequence of the Hepatitis B Virus Genome Elicit Antibodies Reactive With the Native Envelope Protein of Dane Particles", *Proc. Natl. Acad. Sci., 78*, 3403–3407 (1981).

Male, et al., *Advanced Immunology*, generally and Chapters 11–14, J. B. Lippincott Co., Philadelphia, PA (1991).

Yearout, "Prevention and Treatment of Aspergillosis by Vaccination: A New Protocol", *Proceedings Association of Avian Veterinarians*, pp. 139–144 (1988).

PCT Search Report for PCT/US95/01304 (mailed May 4, 1994).

Merrifield, "Solid Phase Peptide Synthesis. I. The Synthesis of a Tetrapeptide", *Science, 85*, 2149–1254 (1963).

Niemi, et al., "Evaluation of Ethylene–Vinyl Acetate Copolymer as a Non–Inflammatory Alternative to Freund's Complete Adjuvant in Rabbits", *Laboratory Animal Science, 35(6)*, 609–612 (1985).

Radomsky, et al., "Controlled Vaginal Delivery of Antibodies in the Mouse", *Biology of Reproduction, 47*, 133–140 (1992).

Roitt, et al., *Immunology*, generally and Chapters 16–17, J. B. Lippincott Co., Philadelphia, PA (1989).

Ulmer, et al., "Heterologous Protection Against Influenza by Injection of DNA Encoding a Viral Protein", *Science, 259*, 1745–1749 (1993).

Van Rooijen, et al., "The Secondary Immune Response Against Liposome Associated Antigens", *Immun. Comm., 10(1)*, 59–70 (1981).

Wagegg et al., "Ferric Citrate Transport in *E. coli*," *J. Bacteriology* 145:161 (1981).

Neilands, J.B., "Microbial Envelope Proteins Related to Iron," *Ann. Rev. Microbiol.* 36:285 (1982).

Crichton, R.R., "Inorganic Biochemistry of Iron Metabolism," pp. 59–76, Ellis Harwood Limited Ch. Chest, West Sussex, P019, 1EB, England (1991).

Mascoplatt, C.C., "Regualtion of immune response in neonatal piglets by maternal antibody," *Int. Arch. Allergy. Appl. Immunol.* 54:165 (1977).

METHOD OF INDUCING AN IMMUNE RESPONSE IN A YOUNG ANIMAL

CROSS-REFERENCE TO RELATED APPLICATION

This is a continuation of U.S. patent application Ser. No. 08/272,116, filed Jul. 7, 1994, now U.S. Pat. No. 5,538,733.

BACKGROUND OF INVENTION

To properly protect a herd or flock of animals from bacterial and viral infections, it is important that the animals maintain a level of immunity against a pathogen at the point when effective passive immunity from circulating maternal antibodies is lost. In mammals, a fetus receives maternally-synthesized antibodies while in utero which confers passive protection to the fetus. In the avian species, immunity is transferred from the hen via the egg, and the progeny in the first few months of life are protected against toxins, viruses and pathogenic bacteria. The levels of these maternal antibodies gradually decline as the newborn begins to synthesize its own antibodies.

The first exposure of an animal to a particular immunogen triggers a priming response. After initial contact with an immunogen, there is a latent period before antibody to that immunogen is detectable in the serum, generally about 1–2 weeks, during which time T and B cells make contact with the immunogen, proliferate, differentiate, and secrete antibody which then increases exponentially in the serum of the animal, reaches a steady state and then, as the immune response shuts down, decreases in concentration in the serum. This priming contact with an immunogen leaves the immunized animal with a cellular memory of the contact such that, upon a second, later contact with the immunogen, a secondary or anamnestic (memory) immune response is automatically triggered in which the lag phase is considerably shorter and the antibody appears much faster and at a higher concentration in the serum. This capacity to make a secondary response provides an advantage to an animal that survives the first contact with an invading pathogen.

Maternal antibody, while capable of providing passive protection to the neonate against a variety of infectious agents or their toxins, may also interfere with the animal's active response to an immunogen by reacting with and tying up the immunogen. As a result, administration of a priming dose of an immunogen to stimulate active immunity in the newborn must be delayed until the level of circulating maternal antibodies has decreased.

To provide continuous coverage so that immunity is maintained after the disappearance of maternal antibodies, the herd may be immunized en masse when all animals have lost passive immunity. A drawback of this approach is that there will be a certain percentage of animals who lose immunity before the rest of the group and are therefore vulnerable during the interim. Another approach is to vaccinate an animal with an immunogen repeatedly from day one until they are found capable of responding, but the stress on the animal and expense for the breeder prohibits this tactic. Yet another approach is to administer to a young animal, a priming dose of an immunogen in a preparation that will present the immunogen in a slowly dissipating material. Examples of such preparations are an injectable water-in-oil emulsion containing live virus, a suspension of an antigen in Freund's complete adjuvant or phosphatidylcholine (egg-lecithin)- or cholesterol-based liposomes containing an entrapped immunogen. However, such preparations do not provide adequate long-term delivery of an immunogen and may cause adverse reactions such as granuloma formation. There is also the risk of the person administering the injection accidentally injecting themselves with the preparation, resulting in an adverse reaction from the injected ingredients. For example, injecting mineral oil into a human finger, or other tissue or body part, will cause severe reaction and may result in the loss of tissue or worse.

Therefore, it is an object of the invention to provide an effective method for priming the immune system of a young animal to achieve a virtually immediate active immune response to infection by a pathogenic organism at the point where such protection is no longer provided by maternal antibodies, without irritation or undue stress caused to the animal. Another object is to provide an effective method for immunizing a large number of animals.

SUMMARY OF THE INVENTION

These and other objects are achieved by the present invention which is directed to a method of priming an immune response in a young animal by administering a biocompatible and non-toxic solid phase implant containing an immunogenic agent. The implant is administered to the animal at about 1–90 days of age in the presence of circulating maternal antibodies, and provides extended sustained delivery of a priming dose of the immunogenic agent into surrounding tissue fluids in the presence of circulating maternal antibodies. A preferred application is the administration of the implant to a one-day old animal.

Advantageously, the present method provides a system for delivering a priming dose of an immunogen to a young animal in the presence of circulating maternal antibodies over an extended time so that the animal will produce a secondary active immune response substantially immediately upon contact with the immunogen when passive protection is no longer provided by circulating maternal antibodies. The priming dose of the immunogen released from the implant is effective to elicit a secondary immune response in the animal to increase the anti-immunogen antibodies to an antibody titer of about 10–1000, or an about 5–100 fold increase in antibody titers.

A preferred implant matrix is made of a biocompatible, biodegradable, bioabsorbable and/or bioerodible polymeric material that will become gradually disintegrated by the animal's system through enzymatic, chemical and/or cellular hydrolytic action, and release the immunogen for sustained delivery into surrounding tissue fluids over an about 1–90 day period. The implant may be formulated, for example, from cholesterol, cellulosic polymers, polylactide, polycaprolactone, polyglycolide or other like polymers or copolymers thereof. The implant may include immunostimulants such as aluminum hydroxide, muramyldipeptide, lipophilic amines, saponins, Freund's incomplete adjuvant (FIA), polymeric adjuvants, among other adjuvants. The implant may also contain an immunomodulator such as a cytokine, complex carbohydrate, and the like to enhance or modulate the immune response, and other additives as desired, such as preservatives, buffering agents, and the like.

The immunogen may be any substance that is structurally and/or functionally capable of stimulating an immune response in an animal, and which may be incorporated into and subsequently released from the implant matrix into surrounding tissue fluids. The immunogen may be in the form of a whole bacterial cell or viral particle, or an isolated and/or substantially pure immunogenic molecule derived therefrom such as a cell surface glycoprotein, sphingolipid and the like; a toxin, allergen, hormone, or anti-idiotype; or a synthetic polypeptide, and the like.

The implant may be administered to the animal by subcutaneous or intramuscular implantation, preferably through the use of an injection gun as known and used in the art, which accommodates administering the implant to a large number of animals within a short period of time. Once implanted, the matrix provides for the sustained release of the incorporated immunogenic agent over an about 1–90 day period into the surrounding tissue fluids of the animal.

Advantageously, the present method of priming an animal by administering an immunogen-containing implant into the animal provides for enhanced immune levels at the point of transition between maternal antibodies and active production of antibodies. The present method provides a means for immunizing a young animal, particularly an animal at one day of age, easily and with a minimal amount of stress placed on the animal, and without adverse reactions such as granuloma formation, and the like.

BRIEF DESCRIPTION OF THE DRAWINGS

FIG. 1A shows the serological profile of maternal antibody to NDV between placebo and vaccinated birds (placebo=▦; NDV-60 day=■). FIG. 1B shows the immune response to NDV after challenge using a 60-day release metabolizable implant (placebo=▦; NDV-60 day=■).

DETAILED DESCRIPTION OF THE INVENTION

Figure 1A:
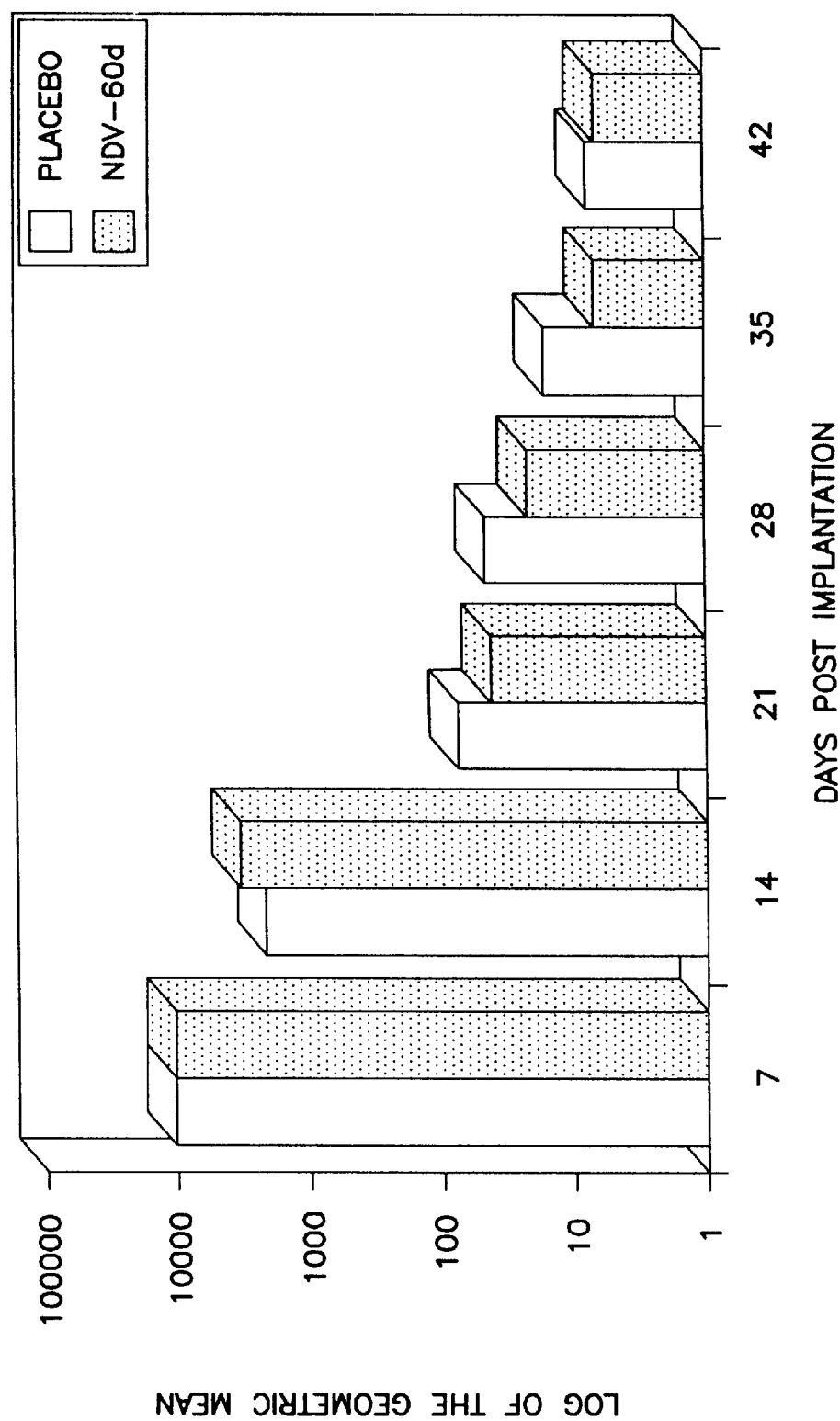
FIGS. 1A and 1B are graphic depictions of the immune response to New Castle Disease (NDV) virus in turkey poults administered a 60-day release, cholesterol-based, metabolizable implant at 1-day of age.

The present invention provides a method for priming an immune response in a 1–90 day old animal, in the presence of circulating maternal antibodies, by employing a biocompatible implant containing an immunogenic agent. According to that method, a continuous amount of the immunogenic agent effective to provide a priming dose of the immunogen is maintained in the circulatory system of the animal by its release from the implant matrix into the tissue fluids of the young animal. The continuous presence of a priming dose of the immunogen provides an effective way of priming a young animal so that a secondary immune response to a pathogenic infection is stimulated substantially immediately when passive protection by maternal antibodies against the pathogen is no longer effective.

As used herein, the term "substantially pure" means that the immunogen has been separated from its natural association with other constituents such as proteins, lipids, and other like substances and elements of a bacterial cell, viral particle and the like. The term "biodegradable" means that the implant matrix will degrade over time by enzymatic or hydrolytic action, or other like mechanism in the animal's body. By "bioerodible," it is meant that the implant will erode or degrade over time by the contact with surrounding tissue fluids, cellular activity and the like. By "bioabsorbable," it is meant that the implant matrix will break down and be absorbed by a cell, tissue, and the like, within the animal's body. By "biocompatible," it is meant that the implant matrix does not cause substantial tissue irritation or necrosis at the implant site.

Implant Matrix

The implant administered according to the method are those known and used in the art that comprise a biocompatible, non-toxic material. Implants useful in the method have a matrix structure that will allow for incorporation of the immunogenic agent and release of the agent at a desired rate.

A preferred implant is made of a biocompatible solid phase polymeric matrix that is bioabsorbable, biodegradable, and/or bioerodible in the body of the animal, and will deliver an immunogen into tissue fluids over an extended period without irritation and adverse effects to the animal. Such polymers allow for the breakdown of the implant during therapy, generally to monomeric subunits that are biocompatible with the surrounding tissue.

Examples of useful polymers for forming a biodegradable, bioabsorbable implant include polylactic acid (PLA), polyglycolic acid (PGA), polycaprolactone, polyanhydride, polyamides, or copolymer thereof such as copolymers of polyamides and polyesters, copolymers of PLA and PGA, and the like. In general, the in vivo life of an implant formulated with such polymers will depend at least in part, on the molecular weight and degree of crosslinking of the polymer in the matrix. Formulations for such matrices are known in the art, as disclosed for example, in U.S. Pat. No. 3,887,699 to Yolles.

Other implants useful in the method include biodegradable, metabolizable, cholesterol-based pellets that provide for slow release of bioactive substances. Cholesterol-based implant matrices are commercially-available, for example, as 21-, 60-, and 90-day implants from Innovative Research, Toledo, Ohio. Other cholesterol-based implants have been described for slow release of biotin and other micronutrients, and proteins, polynucleotides, polysaccharides, for example, U.S. Pat. No. 4,452,775 to Kent; and U.S. Pat. No. 4,326,523 to Wolfrom. Also useful are implants having a peptide/polymer matrix, for example, tyrosine dipeptides and polymers as described in U.S. Pat. No. 4,863,735 to Kohn, and Kohn et al., *J. Immunol. Methods* 95:31–38 (1986), that will degrade to form a product having adjuvant activity for the antigen or other bioactive compound incorporated into the matrix.

Also useful according to the invention is a time-delayed implant, known and used in the art, which upon implantation, will substantially maintain integrity of the matrix for a desired length of time. Preferably, the matrix will remain intact for up to about 3 weeks, or after the level of maternal antibody has significantly declined, at which time the antigen is released from the matrix.

Although not preferred, an implant made of a non-erodible, synthetic polymer, as for example, a hydrogel, a high density polyethylene, or ethylene-vinyl acetate copolymer (EVAC), may be used according to the method for slow delivery of the immunogen. Such implant matrices are described, for example, by Niemi et al., *Laboratory Animal Science* 35:609 (1985) (EVAC); Radomsky et al., *Biol. Reprod.* 47:133–140 (1992) (EVAC); U.S. Pat. No. 5,114,719 to Sabel (EVAC et al.); and U.S. Pat. No. 3,975,350 to Hudgin (hydrogel carrier). However, such implants do not naturally degrade in the body and require surgical removal after the immunogen has been delivered into the body of the animal. In addition, EVAC implants have been shown to cause irritation resulting in necrosis at the implant site. Hydrogels are a polymeric material that swell but will not dissolve in water, and have a structural rigidity imparted by crosslinking agents, as for example, polyhydroxyalkyl methacrylates (P-HEMA), polyacrylamide, polymethacrylamide, polyvinyl pyrrolidone, polyvinyl alcohol (PVA), among others. Low molecular weight substances tend to diffuse relatively quickly through a hydrogel matrix which may be a disadvantage for controlled delivery.

Immunogenic Agent

The method provides sustained and/or timed release of an immunogenic agent from the implant matrix. The immunogenic agent is a substance that is effective in stimulating production of antibodies with specific activity against the immunogenic agent and the pathogenic organism against which the animal is being immunized. The immunogen has a chemical structure which provides for its incorporation into the implant matrix such that over time, the immunogen will be released from the matrix into the adjacent tissue fluids, preferably at a controlled rate. The immunogenic agent may be any antigenic substance that is capable of stimulating an immune response in the animal being treated. The implant may be formulated to include a single immunogen or a mixture of immunogens for immunizing the animal against one or more diseases and/or infections. Preferably, the implant contains about 25–5000 µg/mg of the immunogenic agent preferably about 100–2000 µg/mg, preferably about 250–1000 µg/mg.

The immunogen may be derived from a pathogenic organism such as a bacteria, virus, fungi, mold, protozoans, nematodes, or other organism. The immunogen may be in the form, for example, of whole bacterial cells, whole viral particles, immunogenic subunit molecules or secreted substances derived therefrom, isolated nucleic acid preferably bound to a carrier protein, and the like. Immunogens may be prepared according to conventional isolation and purification methods, and/or by gene expression according to recombinant DNA techniques to make and express a gene encoding all or part of an antigenic peptide chain in an appropriate vector (i.e., vaccinia virus recombinants). Such immunogenic subunits include, for example, subunit vaccine polypeptides, cell membrane glycoproteins, polysaccharides, sphingolipids, lipopolysaccharides, and the like. See, for example, Harlow and Lane, *Antibodies, A Laboratory Manual*, generally and Chapter 5, Cold Spring Harbor Laboratory, Cold Spring Harbor, New York, N.Y. (1988); Male et al., *Advanced Immunology*, generally and pages 14.1–14.15, J.B. Lippincott Co., Philadelphia, Pa. (1991); and Roitt et al., *Immunology*, generally and pages 16.1–17.21, J.B. Lippincott Co., Philadelphia, Pa. (1989).

Also useful are immunogenic synthetic peptides that mimic antigenic peptide sequences. Such immunogens may be synthesized using a solid-phase technique as described, for example, in R. B. Merrifield, *Science* 85:2149–2154 (1963), purified, and optionally coupled to a carrier protein such as muramyldipeptide (MDP), bovine serum albumin (BSA), keyhole limpet hemocyanin (KLH), and the like, using a bifunctional coupling agent such as glutaraldehyde, and the like.

Other useful immunogens are purified, secreted antigen virulence factors, such as toxins, cytotoxins, and the like. Toxin antigens which are detoxified by modifying (toxoids), preferably administered in combination with an adjuvant such as aluminum hydroxide, may be used to stimulate the formation of toxin-neutralizing antibodies. Examples of toxins that may be used as an immunogen include bacterial endotoxins and exotoxins, enterotoxins including heat-labile enterotoxins (LT), heat stable enterotoxins (ST), verotoxin (VT), and the like. Bacterial exotoxin immunogens are secreted into the surrounding medium, and include, for example, diphtheria toxin (*Corynebacterium diphtheriae*), tetanus toxin (*Clostridium tetani*), enterotoxins secreted by *Staphylococcus aureus*, botulinus toxins (*Clostridium botulinum*); and toxins produced by algae such as neurotoxins; and the like. Heat-stable endotoxins, released by autolysis of the bacteria, include, for example, cholera toxins released from the gram negative *Vibrio cholerae,* colicins produced by intestinal bacteria such as *E. coli* (bacteriocin). In brief, toxoids may be prepared, for example, by culturing the bacteria and, after the required growth is attained, filtering the culture to obtain a filtrate containing the toxin (exotoxin), precipitating the toxin from the filtrate using, for example, a concentrated salt solution, washing the precipitated toxin and purifying it by dialysis, and then detoxifying the toxin with formaldehyde. An implant may contain the detoxified toxin (toxoid) plain or with an adjuvant such as alum, aluminum hydroxide or aluminum phosphate. Other toxins may be cell associated and released by rupturing the cell wall by sonication or French pressure, and the like, and the ruptured material then centrifuged and treated as described above.

Another useful immunogen is an allergen such as pollen, danders, mold spores, mycelial fragments, epidermals, and the like, capable of stimulating IgE production.

Also useful is a hapten, or low molecular weight substance such as an antibiotic, drug, peptide, among others, which when conjugated to an immunogenic carrier such as a protein, carbohydrate, lipid, or other like carrier, for example, BSA and KLH, using a bifunctional coupling agent, will induce an immune response directed against the parts of the conjugate. The preparation of hapten immunogens is described, for example, in Harlow and Lane, *Antibodies: A Laboratory Manual,* pages 72–87, Cold Spring Harbor Laboratory, Cold Spring Harbor, New York, N.Y. (1988).

Another immunogen is an anti-idiotype antibody that reacts with the antigen binding site of the idiotype antibody, and structurally mimics the epitope, i.e., contains the internal image of the epitope. The anti-idiotype may be used as an immunogen to induce antibodies against the original epitope. Briefly, anti-idiotypic antibodies may be induced by injecting an antigen into a rabbit and allowing the immune system to produce immunoglobulins. These immunoglobulins are then harvested and injected into a second animal such as a domestic hen. The hen then mounts an immune response to the foreign antibodies with the production of immunoglobulins that mimic the original antigen. Anti-idiotype antibodies may then be isolated from the yolks of eggs laid by the hen by methods known in the art, and used as an original immunogen. A useful method for isolating antibodies from egg yolks is according to the method described in co-pending U.S. patent application Ser. No. 08/188,514, entitled "Method for Purifying Egg Yolk Immunoglobulins." For further discussion of anti-idiotypes as vaccines, see, for example, Bhogal et al., *Crit. Rev. Poultry Biol.* 3:53–68 (1991); and Bhogal et al., *Infection and Immunity* 56:1113–1119 (1988).

The immunogen may also be derived from RNA or DNA viruses. Examples of such viruses include New Castle disease virus (NCDV), hemorrhagic enteriditis virus (HEV), infectious rhinotracheitis virus (IBRV), bovine viral diarrhea virus (BVDV), bovine respiratory syncytial virus (BRSV), hog cholera virus (HCV), equine encephalomyelitis virus (EEV), canine distemper virus, fowl pox virus, rabies virus, avian leukosis virus, turkey virus, infectious bursal disease virus, infectious bronchitis virus, avian influenza virus, avian encephalomyelitis virus, among others. Techniques for the preparation of virus-derived immunogens are known in the art, and described, for example, in Ulmer et al., *Science* 259: 1745 (1993); Male et al., *Advanced Immunology*, pages 14.1–14.15, J.B. Lippincott Co., Philadelphia, Pa. (1989).

Immunogens may also be derived from bacteria such as *Escherichia coli;* Salmonella spp. such as *Salmonella agona, Salmonella blockley, Salmonella enteriditis, Salmonella hadar, Salmonella Heidelberg, Salmonella montevideo, Salmonella senftenberg, Salmonella cholerasuis;* Pasteurella spp. such as *Pasteurella haemolytica* and *Pasteurella multocida;* Pseudomonas spp. such as *Pseudomonas aeruginosa;* Klebsiella spp. such as *Klebsiella pneumoniae;* Actinobacillus spp. such as *A. pleuropneumoniae,* Haemophilus spp. such as *H. parasuis;* Streptococcus spp. such as *S. suis;* Bordetella spp. such as *B. bronchiseptica, B. avium;* among other gram negative bacteria. Examples of gram positive bacteria from which useful immunogens may be derived include Staphylococcus spp., Streptococcus spp., Erysipelothrix spp., Clostridium spp., among others.

The immunogenic agent may also be derived from a fungi or mold such as *Aspergillus flavus, Aspergillus fumigatis,* Penicillium spp., Fusarium spp., Candida spp. such as *C. Trichophyton* spp., Rhizopus spp., and other fungi and molds; protozoa such as Treponema, Toxoplasma, Cryptococcus, Coccidia, Histomoniasis, Hexamitiasis, Giardia, among others; spirochetes such as Borrelia spp; nematodes including Ascaris spp., Trichinella spp., and the like, helminthes such as flukes, tapeworms, among others; and other like pathogenic organisms. Methods for preparing immunogens derived from fungi, molds, protozoa, nematodes, and helminthes are known in the art, and described, for example, by Douglas R. Yearout, 1988 *Proc. Assoc. of Avian Veterinarians,* pages 139–144 (1988) (aspergillus).

A useful immunogenic agent is a siderophore receptor protein (SRP) which is a protein or subunit immunogenic peptide of the protein derived from the outer membrane of a gram-negative bacteria or other pathogenic organism such as a mold or fungus, that will bind a siderophore, or iron-binding protein. Implants containing an SRP immunogen can be administered to elicit an immune response in an animal with the production of anti-SRP antibodies that react with SRPs of the same organism from which the SRP immunogen was derived or cross-react with a SRP of a pathogenic organism of a different strain, species or genus. Examples of siderophore receptor proteins are hydroxamates and phenolates such as aerobactin, enterochelin, citrate, multocidin, ferrichrome, coprogen, mycobactin, and the like, or an immunogenic fragment thereof, that will stimulate production of anti-SRP antibodies.

Siderophore receptor proteins having a molecular weight of about 72–96 kDa, as determined by SDS-PAGE, have been isolated from *E. coli,* Salmonella spp., Pasteurella spp., Pseudomonas spp., and Klebsiella spp. An implant may be formulated to contain, for example, one or more SRPs derived from a serotype of *E. coli* such as *E. coli* serotype 01a, 02a and/or 078 (American Type Culture Collection (ATCC), Bethesda, Md. ATCC Accession No. 55652, on Jan. 3, 1995), the SRP having a molecular weight of about 89 kDa, 84 kDa, 78 kDa or 72 kDa (SDS-PAGE), and effective to stimulate antibodies immunoreactive with the *E. coli* from which the protein is derived and a second gram-negative bacteria such as a species of Salmonella, Pseudomonas, Klebsiella, and/or Pasteurella. Another useful implant may include one or more SRPs derived from a species of Pasteurella, having a molecular weight of about 96 kDa, 84 kDa or 80 kDa; and/or a species of Salmonella having a molecular weight of about 89 kDa, 81 kDa or 72 kDa. In brief, to obtain SRPs for use as immunogens, the SRP-producing organism is cultured in a medium that lacks iron or includes an iron chelating agent and, after harvesting, the SRPs are separated from the organism's outer membrane and purified by treating with an anionic detergent, preferably sodium dodecyl sulfate (SDS) and under non-reducing conditions, as described, for example, in co-pending U.S. patent application Ser. No. 08/194,094 entitled "Active Immunization using a Siderophore Protein."

Yet another implant useful in the present method is one that is formulated to contain vasoactive intestinal peptide (VIP), or an immunogenic fragment thereof. VIP is an about 28 amino acid, synthetically produced peptide, that has been shown to control the release of prolactin in a hen. This, in turn, inhibits nesting behavior, or broodiness, of a hen. VIP is commercially available, for example, from Peninsula Laboratory, Inc., Belmont, Calif. Active immunization by injection with neutralized, endogenous VIP in Freund's incomplete adjuvant has shown a decrease in circulating prolactin and elimination of nesting behavior in hens. However, such injections induce severe granuloma formation and cause added stress to the hen. Surprisingly, the present method of administering a VIP preparation formulated as a metabolizable implant for slow release into the hen has been shown to effectively immunize hens without inducing granuloma formation or other adverse reactions.

In brief, a VIP implant may be prepared by linking the VIP to a carrier protein such as KLH or BSA by means of a bifunctional coupling agent such as m-maleimidobenzoyl-N-hydroxysuccinimide (MBS), carbodiimide, bis-diasotized bensidene (BDB), among others, as described, for example, in Francis et al., *J. Gen. Virol.,* 66:2347–2354 (1985). Preferably, the VIP-KLH conjugate is incorporated into a metabolizable implant material, preferably a cholesterol-based material, which provides sustained release of an effective amount of VIP from the implant matrix into the tissue fluids of the hen to suppress the release of prolactin in the bird. This, in turn, maintains egg production by inhibiting nesting behavior in the hen. The VIP implant is formulated to contain about 25–5000 $\mu$g VIP per mg of the implant matrix, preferably about 25–1000 $\mu$g/mg, and to provide a rate of release of VIP from the matrix of about 0.01–2 $\mu$g/kg weight of the hen per day, preferably about 0.15–1 $\mu$g/kg/day. The hen may be treated to receive VIP over an about 1–210 day period, using one or more VIP-containing implants. A preferred implant contains about 16 µg/mg, and provides a release of about 2.5–3 µg/day in a 30 lb (13.6 kg) hen.

Adjuvants

The implant may include physiologically-acceptable adjuvants as desired to enhance the immune response in the animal. Such adjuvants include, for example, aluminum hydroxide, aluminum phosphate, Freund's incomplete adjuvant (FIA), liposomes, immunostimulating complex (ISCOM), muramyldipeptide (MDP), polysaccharides such as Acemann, and the like. Preferred adjuvants are Al(OH)$_3$ combined with the antigen at about 0.5%, and FIA combined with the immunogen at a ratio of about 1:1. Preferably, where included, the implant matrix comprises about 0.01–10 wt-% of an adjuvant.

Additives

The implant may be formulated with one or more additives to maintain isotonicity, physiological pH and stability, for example, a buffer such as physiological saline (0.85%), phosphate-buffered saline (PBS), citrate buffers, Tris (hydroxymethyl aminomethane (TRIS), Tris-buffered saline and the like, and/or a preservative such as thimersol, formalin, glutaraldehyde, or an antibiotic, for example, neomycin or streptomycin, and the like.

It is also envisioned that the immunogen may be combined with a biocompatible, and optionally synergistic, immunomodulator that cooperatively stimulates antibody production, as for example, recombinant cytokines such as TGF-beta, interferons, activating factors, chemoattractants, interleukins such as IL-1, IL-2, IL-4, IL-5, IL-6, complex carbohydrates such as Acemann (available commercially from Solvay), and other like substances. Immunomodulators are described, for example, in Hudson and Hay, *Practical Immunology*, pages 423–441, Blackwell Scientific Publications, London (1989); and Male et al., *Advanced Immunology*, pages 11.1–11.16, J.B. Lippincott Co., Philadelphia, Pa. (1991).

The matrix may optionally be formulated to include a soluble or insoluble pore-forming agent that will dissipate from the matrix into surrounding tissue fluids causing the formation of pores and/or channels throughout the implant matrix. Examples of such pore-forming agents include sodium chloride and other salts; carboxymethylcellulose, polyethylene glycol and other polymers; starch, glucose and other carbohydrates; amino acids and low molecular weight non-immunogenic proteins and the like. The implant matrix may be formulated to include about 0.05–65 wt-% of a pore-forming agent.

Dosage and Administration

The implant may be used to immunize domestic fowl and other animals such as livestock, horses, companion animals such as cats and dogs, and humans, against infection caused by one or more pathogenic organisms such as a virus, gram-negative bacteria, fungi, mold, and the like. Choice of the particular formulation will depend upon the condition to be treated and the desired release rate, which choice is made by an animal-care professional.

The implant is formulated with an amount of the immunogenic agent effective to provide a desired priming function for the animal's immune system. The "effective amount" of the immunogenic agent included in the matrix is according to the desired release profile, the concentration of immunogen required for a desired priming effect, and the period of time over which the immunogen is to be released. Factors bearing on the vaccine dosage include, for example, the age and weight of the animal. Ultimately, the amount of the immunogen included in the implant is determined by an animal care professional. There is generally no maximum amount of the immunogenic agent that is incorporated into the solid matrix, except for physical limitations that allow the immunogenic agent to be held within the matrix and released in a predetermined manner. Generally, the implant is formulated to contain about 25–5000 µg of the immunogenic agent per mg of the implant matrix, preferably about 100–2000 µg/mg, preferably about 250–1000 µg/mg.

Advantageously, the present method provides for the continuous delivery of an immunogenic agent into the circulatory system of the animal as the level of circulating maternal antibodies diminishes over time and becomes insufficient for providing passive protection against infection by a pathogen. The continuous presence and amount of the immunogenic substance released from the implant matrix provides a priming dose of the antigen effective to stimulate an immune response in the animal in the presence of decreasing maternal antibody titers, substantially immediately upon challenge by a pathogenic bacteria, virus or other organism. In avian species an about 60- to 90-day release implant containing the immunogen will be suitable for delivery of the immunogen, while in mammals, an about 90-day implant is preferred.

The in vivo release rate and extent of release of the immunogenic agent from the solid implant matrix may be effectively controlled and optimized, for example, by varying the matrix formulation according to the desired duration or time interval for maintaining the solid matrix within the implant site, and by varying the type and amount of adjuvants and additives, such as plasticizing agents, and by the size, shape, porosity, solubility and biodegradability of the matrix, among other factors, according to practices known and used in the art. The release of the immunogen from the matrix may also be varied according to the form and solubility of the immunogenic agent in tissue fluids, the distribution of the immunogen within the matrix, among other factors.

The implant is formulated to release a linear dosage amount of the immunogenic agent into the body of the animal over a period of about 1–90 days, preferably about 1–60 days. The release is based on the biodegradability, bioabsorbability and/or bioerodibility of the implant matrix in the body of the animal. For example, a cholesterol-based 60-day release implant pellet (Innovative Research) containing about 25–5000 µg of protein antigen per mg implant matrix, for example, *E. coli* siderophore protein antigen, maintaining a linear release, will release on a daily basis, about 0.4–83 µg/day of protein immunogen. A similar cholesterol-based 21-day implant containing about 5000 µg protein antigen will release about 238 µg/day, and a 90-day implant will release about 56 µg/day. Thus, the implant is formulated to include an amount of an immunogen to provide the desired amount released into the bloodstream over a predetermined time period.

Once implanted, the implant matrix provides for the sustained release of the immunogenic agent into surrounding tissue fluids in the presence of circulating maternal antibodies over the desired time period, preferably disintegrating gradually by the action of the animal's system. The amount of immunogen released from the implant will effectively induce a primary immune response in the animal, so that the animal will respond by the production of antibodies (i.e., secondary immune response) when there is later contact with the immunogen and/or pathogenic organism and the material antibody titer is no longer at a protective level.

Once the animal is primed, a booster is advantageously administered to the animal to stimulate a secondary immune response in the animal. The booster may be in the form of a second sustained-release implant containing the immunogenic agent, an injectable liquid vaccine, a modified live vaccine, a natural exposure to the immunogen/pathogen, or other suitable means. For example, a booster effect in a bird primed with SRPs may come from a natural field exposure with a bacteria that expresses an SRP that will cause a rise in anti-SRP antibody titers. The level of anti-SRP antibodies then remains elevated throughout the life of the bird to protect the animal against lethal challenge by the pathogenic organism. An animal may also be boosted to stimulate a secondary response by injection with an immunogen, for example, a modified live vaccine, at a time after implantation. For example, a 21-day implant containing about 50–500 μg protein antigen and having a release rate of about 8.3 μg/day, may be administered to a one-day old turkey poult, and then a booster injection containing about 500–1500 μg protein may be administered to the poult after the expiration date of the implant (i.e., after 21 days), for example, at about 28–42 days after implantation, to stimulate a secondary immune response. The booster may also be provided from the continued release of the immunogen from the implant used for priming the animal, in which case, after the animal has been primed and becomes immunologically mature and decreasing maternal antibody titers no longer provide effective protection, the continued release of the immunogen from the implant may induce active production of antibodies (i.e., secondary response) in the animal.

The amount of immunogen released from the implant to provide a priming response is effective to induce a secondary immune response in the animal upon delivery of the booster immunogen and/or upon challenge by a pathogenic organism resulting in an about 5–50 times higher antibody titer over pre-challenge antibody titers, as measured by Enzyme Linked Immunosorbent Assay (ELISA) assay, more preferably an about 25–100 fold increase, within about 12–48 hours of receiving the booster and/or challenge, preferably within about 6–24 hours. Preferably, the active antibody titer after the booster or post-challenge, is about 10–1000, preferably about 50–500.

In a preferred method, the serological profile of maternal antibody to a particular immunogen is monitored by flock profiling the vaccinated animals by immunoassay, preferably using a direct ELISA as known and used in the art, for example, a commercially-available ELISA kit for the antigen being assayed. The booster is advantageously administered when the maternal antibody titers have declined to a level at which there is inadequate protection provided against infection by a pathogenic organism, for example, to a titer about 5–10% of peak measurement (i.e., an antibody titer of about 50–100 following a peak titer of 1000). The animal is then boosted to elicit a secondary immune response which is then monitored by testing blood samples by immunoassay. For example, the primary immune response to siderophore receptor protein immunogen(s) (SRPs) can be monitored by vaccinating a group of birds at about 3-weeks of age and testing blood samples at about 5-day intervals for about 20 days. At twenty days post-implantation, birds may then be intramuscularly boosted with E. coli 078, a gram-negative bacteria that expresses four SRPs on its surface. The birds that have been vaccinated against the proteins will then mount a secondary immune response to the proteins. This response can be monitored by taking blood samples from the birds at about 2–4 day intervals and determining the antibody response by ELISA using SRPs as the capture molecule to react with antibodies specific for SRP.

To determine whether the secondary antibody response is protective, a quantitative clearance may be performed by estimating the number of E. coli in organs of the animal. For example, at 24-hour intervals after challenge, the liver and spleens may be aseptically removed from a limited number of animals in the group (vaccinated and non-vaccinated), macerated, and then standard plate counts performed to enumerate the number of bacteria per gram of tissue. The data from the vaccinated birds are compared to non-vaccinated birds, and extrapolated to the remaining animals in the group.

Administration of the implant is ultimately done under the wisdom and protocol of a veterinarian or other animal-care professional. The implant is advantageously and preferably subcutaneously implanted in a 1-day old animal. The implant may also be administered to a young animal up to about 90 days of age, preferably about 1–60 days of age, preferably about 1–25 days of age. Implantation is achieved by a suitable method known and used in art, for example, by surgical incision, or preferably by the use of a commercial injection gun.

The invention will be further described by reference to the following detailed examples, wherein the methodologies are as described below. These examples are not meant to limit the scope of the invention that has been set forth in the foregoing description. Variation within the concepts of the invention are apparent to those skilled in the art. The disclosures of the cited references, patents and co-pending patent applications throughout the application are incorporated by reference herein.

EXAMPLE 1

Priming a 1-day old Poult Against Infection by New Castle Disease Virus (NDV)

Forty 1-day old turkey poults were each administered a 60-day release, cholesterol-based, metabolizable implant (10 mg; Innovative Research, Toledo, Ohio) by subcutaneous injection using an injection gun. Twenty of the poults, i.e. test birds, were implanted with an implant loaded with 10,000 virus particles/implant of New Castle Disease (NCD) virus (LaSota strain) (Solvay Animal Heath, Mendota Heights, Minn.). The stock virus was resuspended in buffered saline and 0.6 ml of β propiolactone (Sigma) was added to inactivate the virus. The killed stock suspension was diluted to 10,000 virus particles and lyophilized with the implant matrix to provide 10,000 virus particles/implant. Twenty of the poults, i.e. control birds, received a placebo implant.

The maternal antibody to NDV was monitored using an NDV-ELISA (commercially available from Kirkegaard & Perry Laboratories, Gaithersburg, Md.). The serological response was monitored at 7-day intervals through 42 days post-implantation. The results are shown in FIG. 1A. At 60 days following implantation, the birds were challenged by intravenously injecting 1-ml of a solution of killed NDV virus at 10,000 virus particles/bird in physiological saline. The serological response to challenge was monitored at 1, 3, and 6 days post-challenge using the above assay.

Figure 1B:
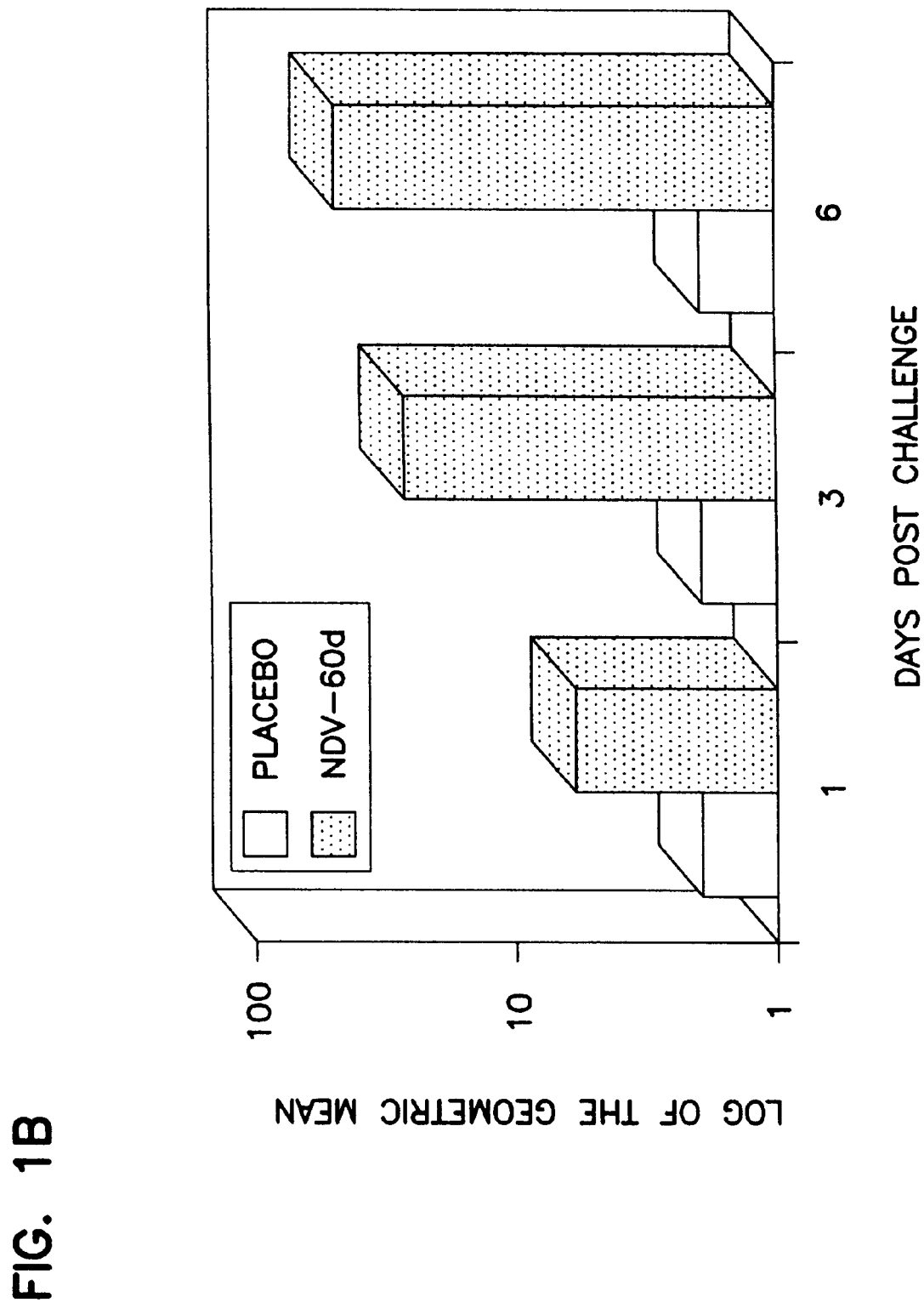

As shown in FIG. 1B, all of the test birds implanted with the immunogen-containing implant sero-converted, and showed a significant secondary immune response after challenge as compared to the non-vaccinated controls.

EXAMPLE 2

Priming a 1-day old Poult Against Infection by Gram-negative Bacteria

A 60-day cholesterol-based matrix of 10 mg, as described in Example 1, was prepared with siderophore receptor proteins derived from *Pasteurella multocida* (turkey isolate; ATCC P-1059) by the following method, as described in co-pending patent application Ser. No. 08/194,040.

*P. multocida* serotype A:3 (700 ml at $10^8$ colonies/ml) was inoculated into a Virtis bench-top fermenter (Virtis, Inc., Gardiner, N.Y.), charged with 20-L of brain-heart infusion (BHI, Difco Laboratories, Detroit, Mich.) containing 50 μgrams/ml of dipyridyl (Sigma Chemical Co., St. Louis, Mo.) at 41° C. This isolate has been shown to produce three siderophore receptor proteins for (M.W. 96 kDa, 84 kDa, 80 kDa) under iron-restrictive conditions. The pH was held constant at 7.4 by automatic titration with 5N NaOH. The fermenter was stirred at 400 rpm. The culture was grown continuously for 18 hours after which the bacteria were removed by continuous-flow centrifugation at 20,000×g at 4° C. using a Beckman (Model J2-21M) centrifuge (Beckman Instruments, Eden Prairie, Minn.). The pelletized bacteria were washed two times with 1,000 ml physiological saline (0.85%) to remove contaminating culture media proteins.

The bacteria were resuspended in tris-buffered saline (TBS) containing 2.0% sodium N-lauroyl sarcosinate (SARKOSYL™, Sigma Chemical Co., St. Louis, Mo.), optical density 5%, 540 nm. The suspension was incubated at 4° C. for 45 minutes with continuous stirring. The cells were then disrupted using a continuous-flow cell sonicator (Banson 450, Danbury, Conn.) at 4° C., with a maximum flow rate of 5 gph. The disrupted cell suspension was centrifuged at 16,000×g for 20 minutes.

The effluent from the continuous-flow cell sonicator containing the outer membrane proteins was collected and concentrated using ethanol precipitation at −20° C. It is understood that the supernatant may also be concentrated by membrane concentration using a high capacity benchtop filtration system, such as Model DC10L with a 30,000 MW cut off spiral cartridge (Amicon, Danvers, Mass.). The concentrated material (10% T at 540 nm) was solubilized using 0.2 percent sodium dodecyl sulfate (SDS) in TBS at pH 7.4.

Figure 2:
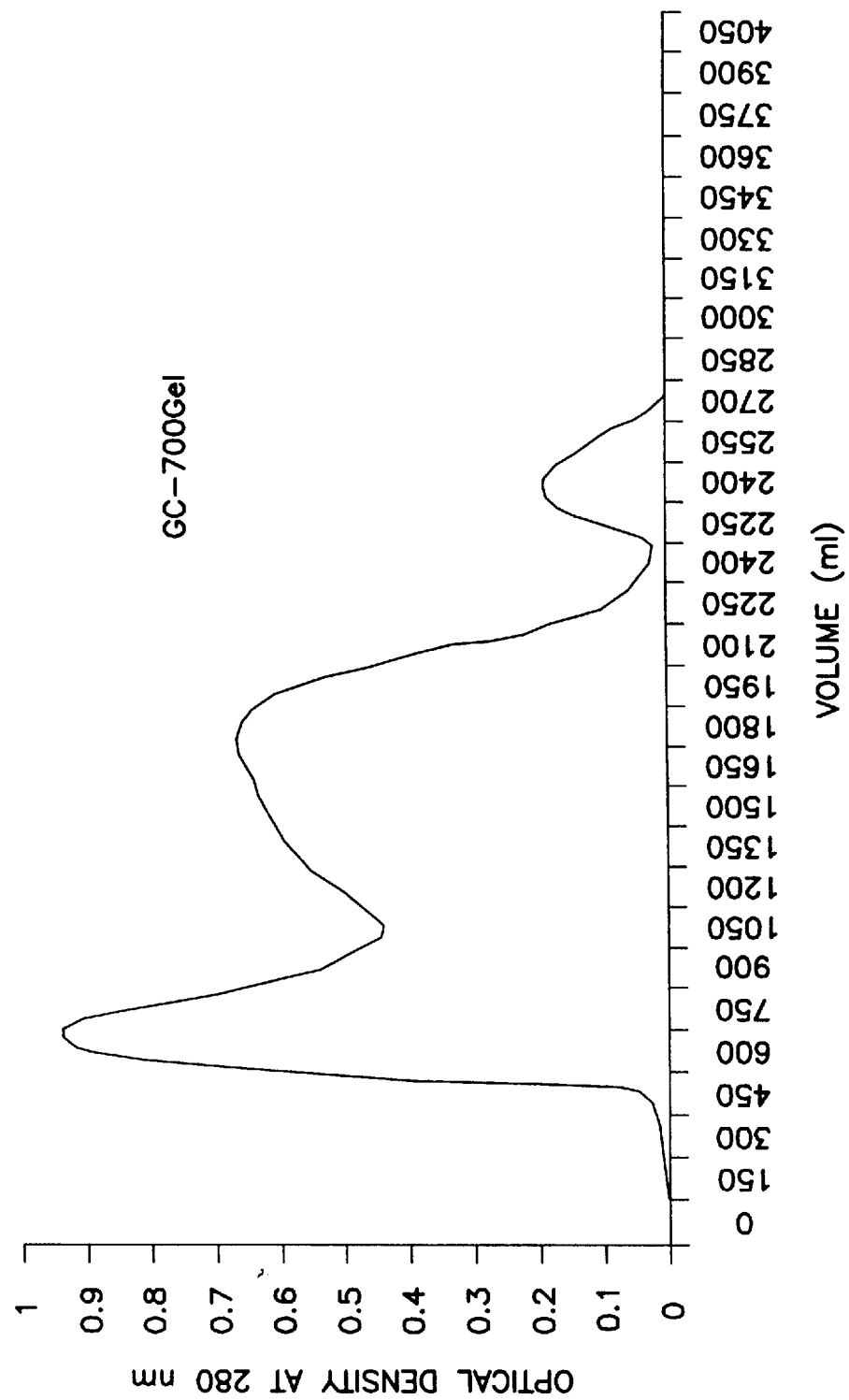
FIG. 2 is a graphic depiction of the elution profile of concentrated, solubilized siderophore receptor proteins isolated from *Pasteurella multocida* serotype A:3 (ATCC 15742).

The elutibn profile of the concentrated material treated with 0.2% SDS is shown in FIG. 2. The solubilized material was applied to a Vantage column (Amicon, Danvers, Mass.) containing 3.2-L of cellufine fast flow GC-700 gel matrix (Amicon, Danvers, Mass.) equilibrated with TBS containing 0.2% SDS at 25° C. Purification of the protein was monitored by UV absorption at 280 nm. Flow rate through the column was 3,000 ml/hr and 20-ml fractions were collected using a UA-5 Detector and Retriever 5 fraction collector (ISCO, Inc., Lincoln, Neb.). Fractions from each peak were pooled and concentrated using a Diaflo ultrafiltration apparatus with a 50,000 MWCO membrane. Concentrated material from each peak was examined by gel electrophoresis. As shown in FIG. 2, peak 1 contained approximately 85% pure siderophore proteins. This solution was ethanol precipitated at −20° C. for 24 hours to remove the SDS, and then resuspended in phosphate buffered saline. The amount of protein was determined using a Pierce BCA protein assay (Pierce, Rockford, Ill.).

The precipitate containing siderophore receptor proteins of *P. multocida* serotype A:3, was resuspended in physiological saline (0.85%) containing 0.1% formalin as a preservative. The protein concentration was 2500 μg/ml.

The implant was loaded with the SRPs from *P. multocida*, such that the implant had a protein concentration of 100 μg/mg or 1000 μg SRP per implant. Twenty 1-day old poults (test birds) were implanted with the 60-day release, protein-loaded implant. Forty birds received a placebo implant, and were used as controls.

Figure 3:
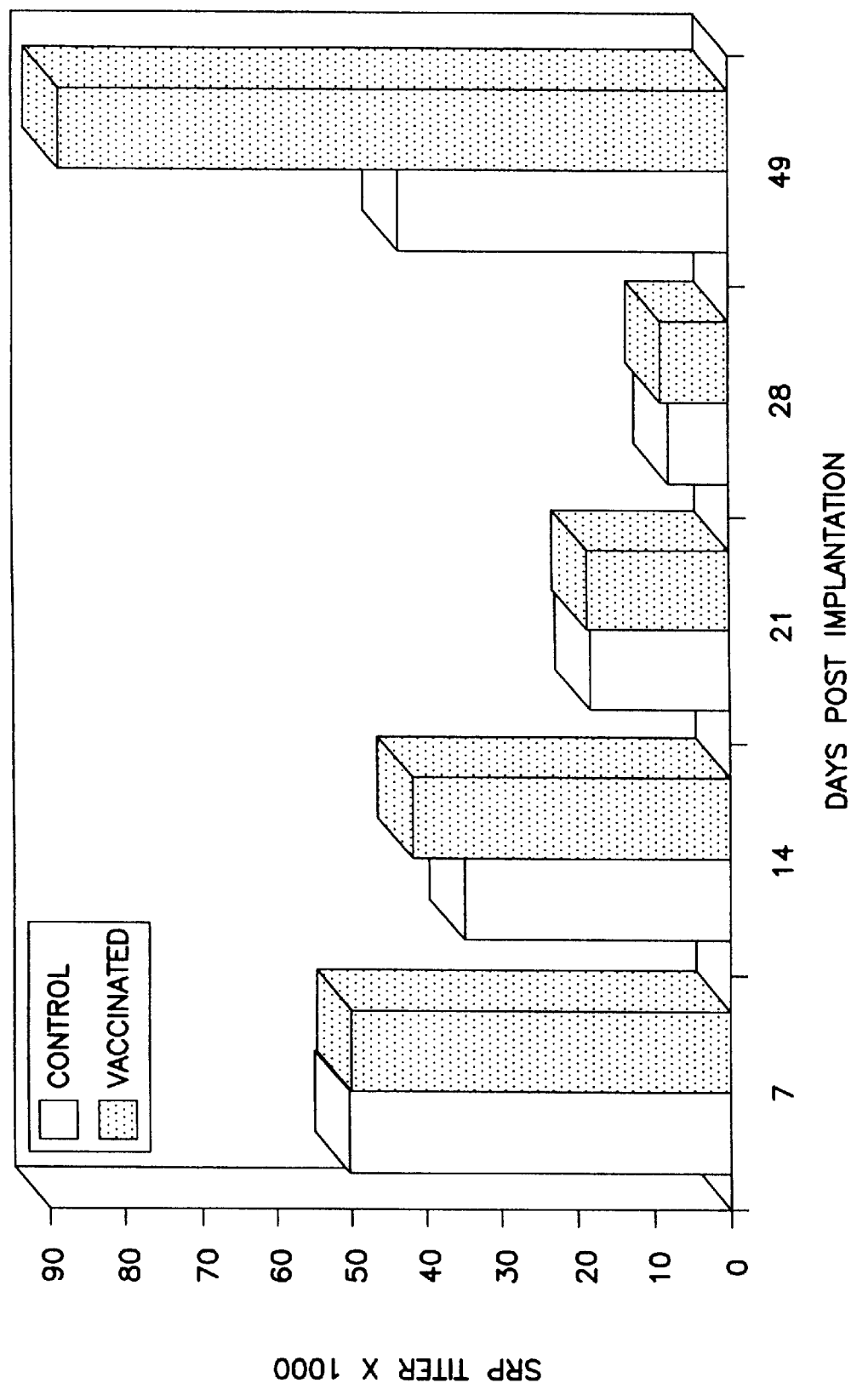
FIG. 3 is a graphic depiction of the immune response to *P. multocida* siderophore receptor proteins in turkey poults administered a 60-day release, cholesterol-based, metabolizable implant at 1-day of age (control=▦; vaccinated=■).

FIG. 3 shows the decay pattern in the maternal antibody to SRPs from 7–28 days in both the vaccinated and non-vaccinated groups. The maternal antibody levels were measured by ELISA using SRPs as the capture molecule. At 49 days after implantation, a rise in SRP titer was observed in both groups. This increase in SRP titers was likely due to a non-specific challenge with an organism that expressed SRPs that have been shown to cross-react with the SRPs from *P. multocida*. The birds in the vaccinated group showed a significantly higher SRP titer in comparison to the non-vaccinated control birds. This increased response indicates that there was a priming effect by the release of SRP immunogen from the implant in the SRP-implanted birds that resulted in a secondary immune response from the natural field exposure with an organism expressing SRPs which acted as a booster to stimulate antibody production.

At 70 days following implantation, all birds were challenged by intramuscular injection of 1-ml of sterile saline containing 659 colony forming units (CFU) of *P. multocida* ATCC P-1059. Mortality was recorded daily for two weeks post-challenge.

Table 1, below, shows the mortality between the vaccinated and non-vaccinated turkeys following challenge with virulent *Pasteurella multocida* P-1059.

TABLE 1

| Number of dead total tested (%) | |
| --- | --- |
| Non-Vaccinated | SRP-Vaccinated |
| 23/38 (61%) | 5/16 (31%) |

Twenty-three (61%) of the non-vaccinated birds died within 14 days after challenge showing only a 39% liveability. In contrast, only 5 out of 16 birds (31%) of the SRP-vaccinated group died, with a liveability of 69%.

These results demonstrate that a vaccine presented to a bird at 1-day of age in the form of an implant matrix and the sustained release of protein immunogen from the implant in the presence of maternal antibody, effectively induced a priming response in the birds to provide protection to a later challenge by a pathogenic organism. In particular, the observed increase in antibody titers when the birds were field challenged at 49 days after implantation, shows that the release of the immunogen from the implant effectively primed the birds in the presence of maternal antibodies so that the birds were capable of producing antibodies in a secondary immune response when maternal antibody titers no longer provided effective protection against the pathogen.

An implant incorporating a siderophore receptor protein (SRP) is useful for achieving clinical efficacy of cross-reactive and cross-protective immunization against two or more different strains, species and/or genera of gram-negative bacteria or other organisms capable of expressing SRPs. An implant containing an SRP reactive with an aerobactin siderophore, an enterochelin siderophore, a citrate siderophore, a multocidin siderophore, and/or a ferrichrome siderophore, may be used to stimulate production of antibodies that cross-react with a number of different bacteria that express one or more of these receptor proteins. The effectiveness of the implant is due, at least in part, to the conservative nature of the outer membrane SRPs which are cross-reactive with siderophores produced by two or more different species, strains and/or genera of Enterobacteriaceae such as *E. coli,* Salmonella, and other gram-negative bacteria within other families such as Pasteurella and/or Pseudomonas.

EXAMPLE 3

Priming with Implant Containing Bovine Serum Albumin

Twelve 1-day old turkey poults were each administered a 21-day release, cholesterol-based, metabolizable implant (10 mg; Innovative Research, Toledo, Ohio). Six of the birds (i.e., test birds) were implanted with the implant loaded with 250 µg/mg bovine serum albumin (BSA) (Sigma). The six remaining birds received a placebo implant with no BSA, and were used as controls. Sero-conversion to BSA was monitored at 7, 21, 35, 49, 56 and 66 days post implantation and compared to the control birds. At 66 days following implantation, the birds were challenged by intravenously injecting 1-ml of a solution of BSA in physiological saline (1000 µg/ml).

Figure 4:
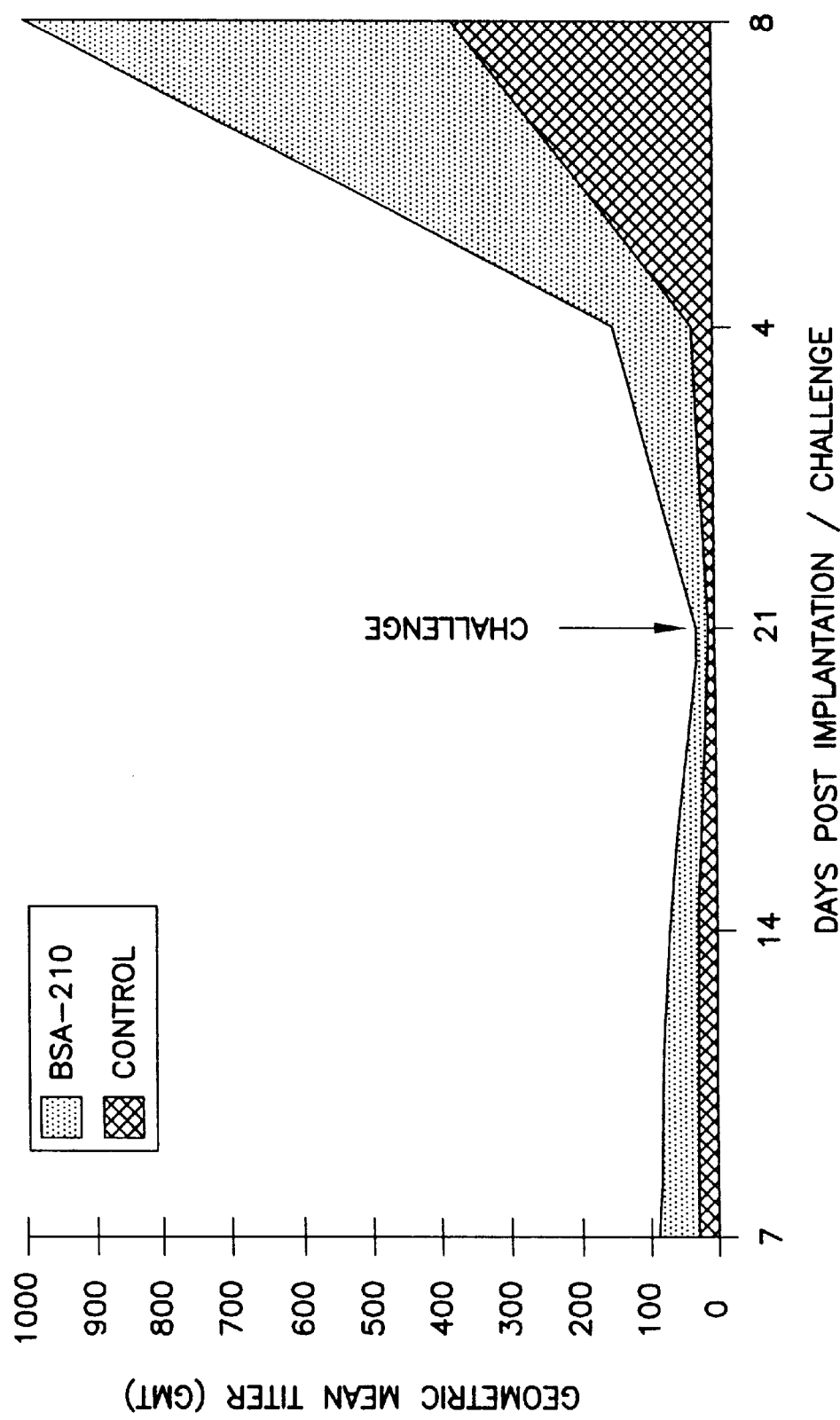
FIG. 4 is a graphic depiction of the immune response to Bovine Serum Albumin (BSA) in turkey poults administered a 21-day release, cholesterol-based, metabolizable implant at 1-day of age (BSA-21 day=▦; control=■).

As shown in FIG. 4, all BSA-implanted test birds sero-converted, and showed a significant secondary immune response after challenge as compared to the non-vaccinated controls.

EXAMPLE 4

Priming 2-week Old Turkeys with Bovine Serum Albumin (BSA)

Twenty-four 2-week old turkeys were equally divided into two groups of twelve and implanted with a cholesterol-based, metabolizable implant as described in Example 1. The first group of birds received a 60-day release implant, six of the birds (i.e., test birds) receiving the implant loaded with 500 µg BSA, and the remaining six birds (i.e., control birds) receiving a placebo implant. The second group of birds received a 90-day release implant, six of the birds (i.e., test birds) receiving the implant loaded with 1000 µg BSA, and the remaining six birds (i.e., control birds) receiving a placebo implant.

Sero-conversion of the birds to BSA was monitored at 7, 21, 35, 49, 56 and 66 days post-implantation and compared to their corresponding controls. At 66 days following implantation, the birds were challenged by intravenously injecting 1-ml of sterile saline containing 1000 µg/ml BSA.

Figure 5:
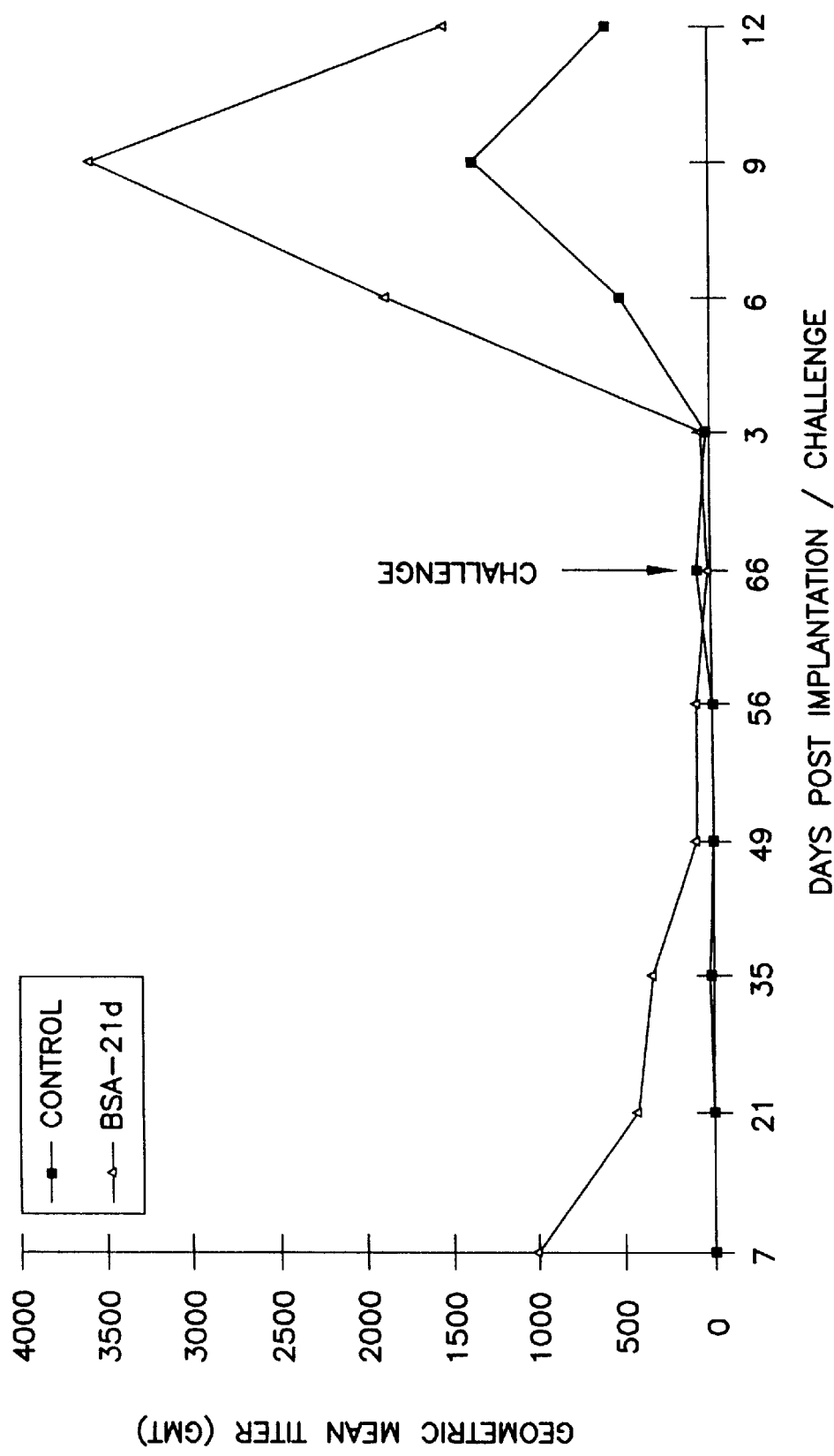
FIG. 5 is a graphic depiction of the immune response to BSA in turkey poults administered a 21-day release, cholesterol-based metabolizable implant at 2 weeks of age (BSA-21 day=—△—; control=—■—).
Figure 6:
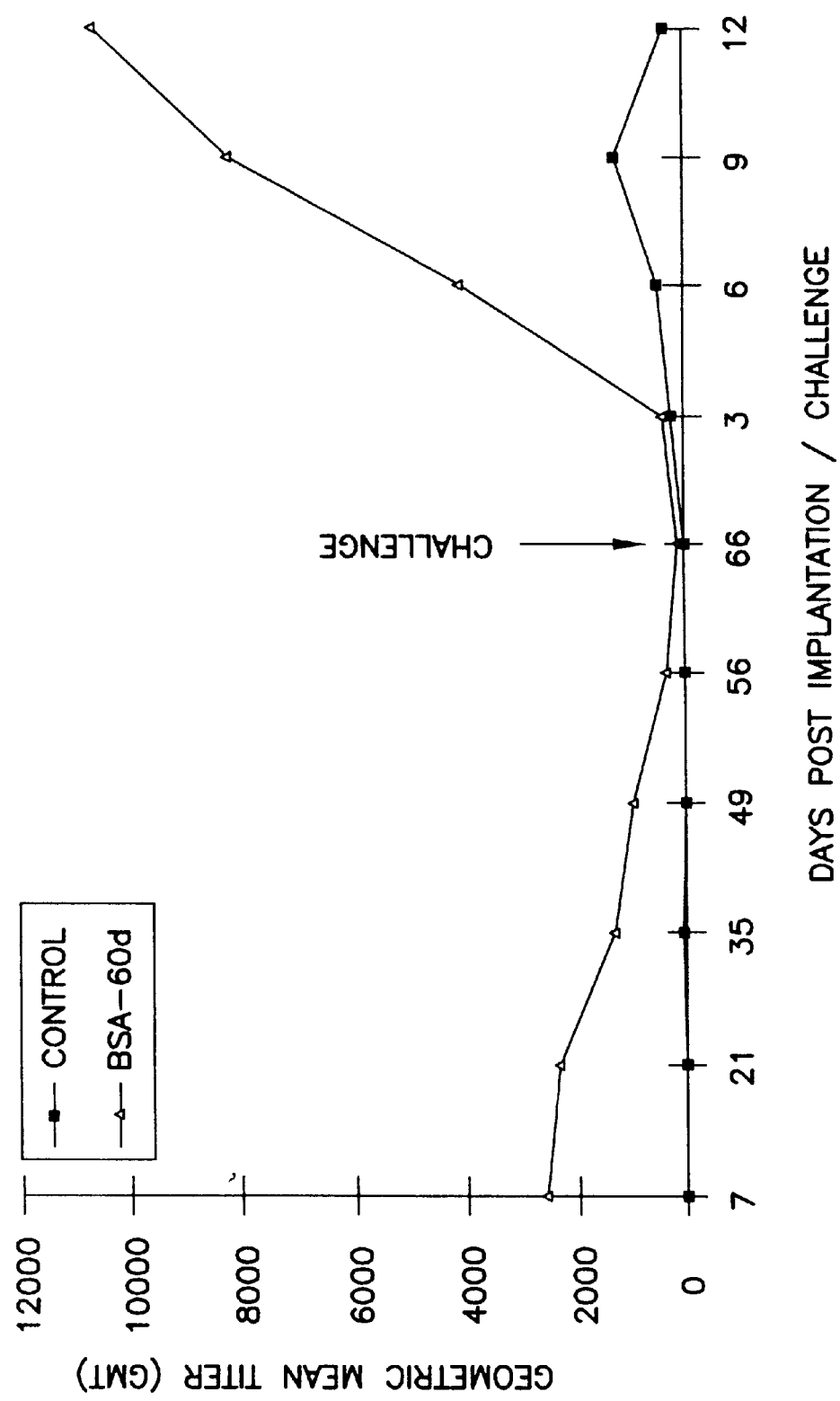
FIG. 6 is a graphic depiction of the immune response to BSA in turkey poults administered a 60-day release, cholesterol-based metabolizable implant at 2 weeks of age (BSA-60 day=—△—; control=—■—).
Figure 7:
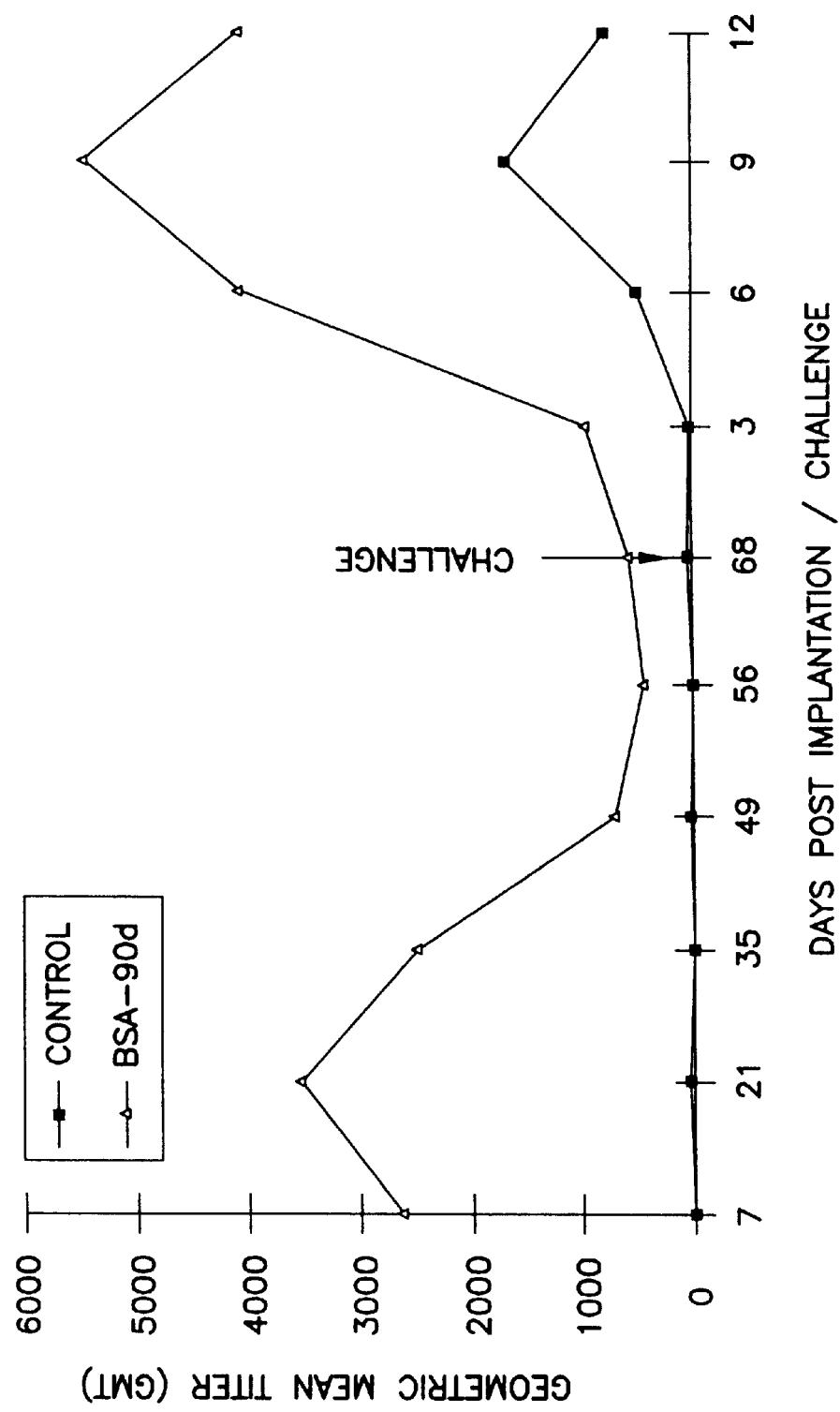
FIG. 7 is a graphic depiction of the immune response to BSA in turkey poults administered a 90-day release, cholesterol-based metabolizable implant at 2 weeks of age (BSA-90 day=—△—; control=—■—).

As shown in FIGS. 5–7, all BSA-implanted test birds sero-converted as compared to the control birds, and showed a significant secondary immune response after challenge as compared to the non-vaccinated controls.

EXAMPLE 5

Priming with Vasoactive Intestinal Peptide (VIP)

A cholesterol-based implant was prepared with vasoactive intestinal peptide, and administered to breeder hens to control broodiness or nesting behavior.

Vasoactive intestinal peptide (1 mg; purified; Peninsula Laboratory Inc., Belmont, Calif.) was conjugated to 1 mg keyhole limpet hemocyanin/MPS at a ratio of (1:1), according to the method of Lerner et al., *Proc. Natl. Acad. Sci.* 78:3403–3407 (1981). Briefly, keyhole limpet hemocyanin (KLH, Calbiochem) and m-maleimidobenzoyl-N-hydroxysuccinimide (MBS, Calbiochem) were dissolved in a carrier by adding 5 mg KLH to 250 ml of 0.05 M phosphate buffer (pH 6.0) and 5 mg MBS to 100 ml N,N,-dimethylformamide (Sigma). Ten µl of the MBS solution and 200 µl of the KLH solution were combined and incubated at 25° C. for 30 minutes. The KLH/MBS suspension was then loaded onto a G-25 column matrix, and fractions absorbing at 280 nm were pooled and used for conjugation.

The VIP (3.6 mg) was solubilized in $dH_2O$ and added to 3.6 mg of the XBS/KLH suspension in 0.05 M phosphate buffer (pH 7.0) at a 1:1 ratio and incubated at 25° C. for 3 hours. The resulting VIP-KLH/MBS conjugate was incorporated into 21- and 60-day release, cholesterol-based, metabolizable implants at 160 µg/capsule (Innovative Research of America Toledo, Ohio).

Twelve 15-week old breeder hens were divided into two groups of six, designated as Groups A and B. In Group A, four birds received the VIP-KLH/MBS conjugate, two birds received the 21-day implant and two birds received the 60-day release implant. The two remaining birds in Group A remained as non-implanted controls. All six birds in Group B received a placebo implant and remained as controls.

At three weeks from the expiration date of the 21-day release implant, the two 21-day implanted birds in Group A each received a 60-day release implant containing 160 µg VIP-KLH/MBS conjugate, giving these birds an additional 60 days of treatment.

Beginning at 22 weeks, the hens began to lay eggs. Eggs were collected from the hens at daily intervals for 10 weeks of production. Over that time, the VIP-treated birds produced 180 eggs. By comparison, the untreated control group produced only 16 eggs in that time period.

FIGS. 5 and 6 represent the daily and weekly egg production between the VIP-treated birds and the non-treated control group. In the VIP group, all four implanted birds went into production. By comparison, the two control birds in this group, under identical conditions, did not lay any eggs. Only two of the six birds in the control group laid eggs. It was also observed that the VIP-containing implants did not induce any granuloma formation or any other adverse reaction in the VIP-implanted birds.

EXAMPLE 6

Priming Turkeys at 1-Day of Age with Hemorrhagic Enteritis Virus (HEV)

Thirty 1-day old turkey poults were each administered a 60-day release, cholesterol-based metabolizable implant. Fifteen of the birds received the implant loaded with $10^3$ $TCID_{50}$ killed HEV particles. The remaining fifteen birds received a placebo implant with no HEV and were used as controls. At seventy days after implantation, all of the birds were challenged by intravenously injecting 1-ml of sterile saline containing $10^2$ $TCID_{50}$ virulent HEV particles. Mortality was recorded daily for two weeks post-challenge.

Table 2, below, shows the mortality between the vaccinated and non-vaccinated birds following an HEV challenge.

TABLE 2

| Numbers of dead/total tested | |
|---|---|
| Non-Vaccinated | Vaccinated |
| 6/15 (40%) | 0/15 |

Six (40%) of the non-vaccinated birds died within 14 days after challenge. By comparison, none of the birds in the vaccinated group died. These results demonstrate that a vaccine presented to a bird at 1-day of age in the form of a metabolizable implant can induce effective protection to a later viral challenge.

What is claimed is:

1. A method for inducing active immunity in an animal against an antigen in the presence of circulating maternal antibodies against the antigen, the method comprising:

administering a biocompatible solid implant having the antigen releasably contained therein during a period when maternal antibodies are circulating in the animal;

the antigen derived from an organism selected from the group consisting of bacteria, virus, fungi, mold, protozoans, nematodes, helminths, and spirochetes;

wherein the solid implant provides release of the antigen into tissue fluids of the animal in an amount effective to stimulate active immunity.

2. The method according to claim 1, wherein the animal is a one-day old animal.

3. The method according to claim 1, wherein the implant is administered to the animal between about 1–90 days of age.

4. The method according to claim 1, wherein the implant is administered to the animal between about 1–25 days of age.

5. The method according to claim 1, wherein the implant delivers the immunogen continuously over an about 1–90 day period.

6. The method according to claim 1, wherein the implant is a delayed release implant that provides release of the antigen at about 1–90 days after being administered to the animal.

7. The method according to claim 1, wherein the animal is selected from the group consisting of livestock, cats and dogs.

8. The method according to claim 7, wherein the livestock is a turkey.

9. The method according to claim 1, wherein the implant is administered to the animal by surgical incision, by subcutaneous injection, or intermuscular injection.

10. The method according to claim 1, wherein a secondary immune response is stimulated by administering a booster antigen in the form of a solid implant or an injectable liquid.

11. The method according to claim 10, wherein the booster antigen is in the form of a modified live vaccine.

12. The method according to claim 10, wherein the secondary immune response provides an about 5–100 fold increase in antigen antibody titers in the animal.

13. The method according to claim 12, wherein the increase in antibody titers is about 6–48 hours after the contact with the booster antigen.

14. The method according to claim 1, wherein the solid implant comprises a polymer that is bioabsorbable, biodegradable, bioerodible, or combination thereof.

15. The method according to claim 14, wherein the polymer is selected from the group consisting of a cellulosic polymer, polylactic acid, polyglycolic acid, polycaprolactone, polyanhydride and polyamide.

16. The method according to claim 1, wherein the solid implant is a cholesterol-based implant.

17. The method according to claim 1, wherein the solid implant comprises a polymer selected from the group consisting of polyhydroxyalkyl methacrylate, polyacrylamide, polymethacrylamide, polyvinylpyrrolidone, polyvinyl alcohol, polyethylene, and ethylene-acetate copolymer.

18. The method according to claim 1, wherein the antigen is selected from the group consisting of peptides, polypeptides, proteins, glycoproteins, polysaccharides, lipopolysaccharides, sphingolipids and toxins.

19. The method according to claim 1, wherein the antigen is derived from a virus or bacterium.

20. The method according to claim 19, where the antigen is derived from a virus selected from the group consisting of New Castle disease virus, hemorrhagic enteriditis virus, infectious rhinotracheitis virus, infectious bursal disease virus, infectious bronchitis virus, avian encephalomyelitis virus, bovine viral diarrhea virus, bovine respiratory syncytial virus, hog cholera virus, equine encephalomyelitis virus, canine distemper virus, fowl pox virus, rabies virus, avian leukosis virus, and avian influenza virus.

21. The method according to claim 19, wherein the antigen is derived from a bacterium selected from the group consisting of *Escherichia coli,* Salmonella, Pasteurella, Pseudomonas, Klebsiella, Actinobacillus, Haemophilus, Streptococcus, Bordetella, Staphylococcus, Clostridia, Erysipelothrix, and Borrelia.

22. The method according to claim 1, wherein the antigen is derived from a fungi or mold selected from the group consisting of Aspergillus, Penicillium, Fusarium, Rhizopus, and Candida.

23. The method according to claim 18, wherein the antigen is a polypeptide capable of functioning in the transport of iron across a cell membrane of an organism.

24. The method according to claim 23, wherein the polypeptide is a siderophore receptor protein reactive with a siderophore selected from the group consisting of aerobactin, enterochelin, citrate, multocidin, ferrichrome, coprogen, and mycobactin.

* * * * *

UNITED STATES PATENT AND TRADEMARK OFFICE
CERTIFICATE OF CORRECTION

PATENT NO. : 5,906,826

DATED : MAY 25, 1999

INVENTOR(S) : EMERY ET AL.

It is certified that error appears in the above-identified patent and that said Letters Patent is hereby corrected as shown below:

Col. 14, line 38, Table 1: "dead total" should read —dead/total—

Col. 16, line 15: "XBS/KLH" should read —MBS/KLH—

Signed and Sealed this

First Day of February, 2000

*Attest:*

Q. TODD DICKINSON

*Attesting Officer*     *Acting Commissioner of Patents and Trademarks*

UNITED STATES PATENT AND TRADEMARK OFFICE
Certificate

Patent No. 5,906,826                                                                        Patented: May 29, 1999

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Daryll A. Emery, Willmar, MN (US); and Darren E. Straub, Willmar, MN (US).

Signed and Sealed this Twelfth Day of June 2007.

<div align="right">

WILLIAM R. DIXON, JR.
*Special Program Examiner*
Technology Center 1600

</div>